(12) United States Patent
Saegusa et al.

(10) Patent No.: US 6,997,035 B2
(45) Date of Patent: Feb. 14, 2006

(54) METHOD AND DEVICE FOR EVALUATING RESTITUTION CHARACTERISTICS OF A GOLF CLUB HEAD

(75) Inventors: Hiroshi Saegusa, Kanagawa Prefecture (JP); Kazunori Ono, Kanagawa Prefecture (JP)

(73) Assignee: The Yokohama Rubber Co., Ltd., Tokyo (JP)

(*) Notice: Subject to any disclaimer, the term of this patent is extended or adjusted under 35 U.S.C. 154(b) by 0 days.

(21) Appl. No.: 10/820,751

(22) Filed: Apr. 9, 2004

(65) Prior Publication Data

US 2004/0200263 A1    Oct. 14, 2004

(30) Foreign Application Priority Data

Apr. 11, 2003  (JP) ............................. 2003-107511
Aug. 7, 2003   (JP) ............................. 2003-289095

(51) Int. Cl.
*G01L 25/00* (2006.01)
(52) U.S. Cl. ..................................... 73/11.01
(58) Field of Classification Search ................ 73/11.01
See application file for complete search history.

(56) References Cited

U.S. PATENT DOCUMENTS

| | | | |
|---|---|---|---|
| 4,928,965 A * | 5/1990 | Yamaguchi et al. ........... 73/574 |
| 6,585,605 B1 | 7/2003 | Erickson et al. ............ 473/282 |
| 6,595,057 B1 * | 7/2003 | Bissonnette et al. .......... 73/579 |
| 6,648,769 B1 | 11/2003 | Lee et al. .................... 473/223 |
| 2002/0183136 A1 * | 12/2002 | Helmstetter et al. ........ 473/345 |
| 2004/0005938 A1 | 1/2004 | Saegusa et al. ............. 473/409 |

FOREIGN PATENT DOCUMENTS

| | | |
|---|---|---|
| JP | 2002-331050 | 11/2002 |
| JP | 2003-24477 | 1/2003 |
| JP | 2003-24478 | 1/2003 |

* cited by examiner

*Primary Examiner*—Max Noori
*Assistant Examiner*—Alandra Ellington
(74) *Attorney, Agent, or Firm*—Finnegan, Henderson, Farabow, Garrett & Dunner, L.L.P.

(57) ABSTRACT

A method for evaluating restitution characteristics of a golf club head with ease and high accuracy compared to conventional methods and devices. The method first acquires a resonance frequency of the impact surface in a mass added state, which is obtained by affixing a mass regulating member having a known mass to the impact surface, and then acquiring a resonance frequency of the impact surface in a non-mass added state, in which the mass regulating member is not affixed to the impact surface, by using a response signal of the impact surface due to the impact vibration; and next computing, by using the resonance frequencies acquired in the mass added state and the non-mass added state, a coefficient of restitution for the impact surface when the impact surface impacts a golf ball.

18 Claims, 8 Drawing Sheets

METHOD AND DEVICE FOR EVALUATING RESTITUTION CHARACTERISTICS OF A GOLF CLUB HEAD

BACKGROUND OF THE INVENTION

1. Field of the Invention

The present invention relates to a method and a device for evaluating restitution characteristics of a golf club head, such as a hollow metallic golf club head, which are used for evaluating restitution characteristics of an impact surface of the golf club head when the golf club head strikes a golf ball.

2. Description of the Related Art

Golf club manufacturers have proposed a variety of golf clubs having golf club heads with good restitution characteristics so that even low-power golfers are capable of driving a golf ball over a long distance. This has been achieved through improvements in, and development of, golf club head structures and materials.

Furthermore, an assessment of the restitution characteristics of a golf club head is made by evaluating a coefficient of restitution e found by a measurement method proposed by the United States Golf Association (USGA), for example. The USGA requires that the golf clubs used in golf competitions have the coefficient of restitution, e, of 0.830 or less.

The coefficient of restitution e is found by impacting a golf ball perpendicularly with respect to the golf ball impact surface (impact surface) of a golf club head placed on a support stand without a golf club shaft. The coefficient of restitution e is computed from the following equation at the time of impact by using a golf ball's inbound velocity $V_{in}$, a golf ball's rebound velocity $V_{out}$, a golf club head mass $M_n$, and a golf ball mass $M_b$.

$$V_{out}/V_{in}=(e \cdot M_h - M_b)/(M_h + M_b)$$

In contrast, a method capable of easily finding the coefficient of restitution of a impact surface of a golf club head from a first resonance frequency of the impact surface is disclosed in JP 2002-331050 A. Impact vibration is performed on the impact surface without impacting a golf ball onto the golf club head.

Furthermore, a method for estimating the coefficient of restitution of a golf club head by inputting a golf model into a golf club head transfer function and a golf ball impact velocity which are obtained experimentally is disclosed in JP 2003-024477 A. Specifically, the coefficient of restitution e is found from a relationship among the above at the time of impact through the golf ball model.

The coefficient of restitution of the golf club head can be found extremely easily and in a short period of time with the method of JP 2002-331050 A, while the coefficient of restitution can also be suitably found with the method of JP 2003-024477. However, it is still strongly desired to find the coefficient of restitution with high accuracy for a variety of golf club heads having impact surface structures that do not possess uniform thickness.

Furthermore, the method of JP 2003-024477 involves the complexity of preparing a golf ball model in advance when finding the coefficient of restitution e.

SUMMARY OF THE INVENTION

An object of the present invention is to provide a method and a device for evaluating restitution characteristics of a golf club head that is capable of computing a coefficient of restitution with ease and high accuracy compared to conventional methods and devices, without using a golf ball model like that used in JP 2003-0244778 A.

This invention provides a method of evaluating restitution characteristics of a golf club head by performing impact vibration through application of an external force to a golf ball impact surface of the golf club head. The method comprises acquiring a resonance frequency of the impact surface in a mass added state, which is obtained by affixing a mass regulating member having a known mass to the impact surface, and acquiring a resonance frequency of the impact surface in a non-mass added state, in which the mass regulating member is not affixed to the impact surface, by using a response signal of the impact surface due to the impact vibration; and computing, by using the resonance frequency obtained in the mass added state and the resonance frequency in the non-mass added state, a coefficient of restitution for the impact surface when the impact surface impacts a golf ball.

The method preferably further comprises, when computing the coefficient of restitution, obtaining a parameter that specifies the resonance frequency of the impact surface in the non-mass added state, in which the mass regulating member is not affixed to the impact surface, and computing the coefficient of restitution of the impact surface when the impact surface impacts a golf ball by using the parameter.

The resonance frequency can be a first resonance frequency of the impact surface. The parameter can be a modal parameter of a resonance mode of the impact surface. Then, the method more preferably further comprises, when computing the coefficient of restitution, obtaining a modal parameter, the modal parameter being one of a modal mass and a modal stiffness, and using the modal parameter to compute the coefficient of restitution.

The response signal can be an acceleration signal of vibrations of the impact surface. Alternatively, the response signal can be a sound pressure signal of the impact surface.

When the response signal is an acceleration signal, then the method preferably further comprises: performing the impact vibration by applying the external force at plural points that are distributed on the impact surface; obtaining, for each of the points, a transfer function for an acceleration signal with respect to the external force; and acquiring as the first resonance frequency of the impact surface a peak frequency at which a peak forms in an identical phase in each obtained transfer function.

This invention also provides a method of evaluating restitution characteristics of a golf club head by performing impact vibration through application of an external force to a golf ball impact surface of the golf club head. The method comprises acquiring resonance frequencies of the impact surface in a plurality of mass-added states, which are obtained by affixing respectively a plurality of mass regulating members having known, mutually differing masses to the impact surface, by using a response signal of the impact surface due to the impact vibration; and computing, by using the resonance frequencies acquired in a plurality of mass-added states, a coefficient of restitution for the impact surface when the impact surface impacts a golf ball.

The method preferably further comprises, when computing the coefficient of restitution, obtaining a parameter that specifies the resonance frequency of the impact surface in the non-mass added state, in which the mass regulating member is not affixed to the impact surface, and computing the coefficient of restitution of the impact surface when the impact surface impacts a golf ball by using the parameter.

The resonance frequency can be a first resonance frequency of the impact surface. The parameter can be a modal parameter of a resonance mode of the impact surface. Then, the method more preferably further comprises, when computing the coefficient of restitution, obtaining a modal parameter, the modal parameter being one of a modal mass and a modal stiffness, and using the modal parameter to compute the coefficient of restitution.

The response signal can be an acceleration signal of vibrations of the impact surface. Alternatively, the response signal can be a sound pressure signal of the impact surface.

When the response signal is an acceleration signal, then the method preferably further comprises: performing the impact vibration by applying the external force at plural points that are distributed on the impact surface; obtaining, for each of the points, a transfer function for an acceleration signal with respect to the external force; and acquiring as the first resonance frequency of the impact surface a peak frequency at which a peak forms in an identical phase in each obtained transfer function.

This invention also provides a device for evaluating restitution characteristics of a golf club head, the device evaluating the restitution characteristics of the golf club head by using a response signal of a golf ball impact surface of a golf club when impact vibration is performed on the impact surface by applying an external force to the impact surface. The device comprises a resonance frequency computing portion that acquires a resonance frequency of the impact surface in a mass added state, which is obtained by affixing a mass regulating member having a known mass to the impact surface, and a resonance frequency of the impact surface in a non-mass added state, in which the mass regulating member is not affixed to the impact surface, by using a response signal of the impact surface due to the impact vibration; and a restitution coefficient computing portion that obtains, by using the resonance frequency in the mass added state and the resonance frequency in the non-mass added state, a coefficient of restitution for the impact surface when the impact surface is impacted by the golf ball.

This invention still also provides a device for evaluating restitution characteristics of a golf club head, the device evaluating the restitution characteristics of the golf club head by using a response signal of a golf ball impact surface of a golf club when impact vibration is performed on the impact surface by applying an external force to the impact surface. The device comprises: a resonance frequency computing portion that acquires resonance frequencies of the impact surface by using a response signal of the impact surface due to the impact vibration, with the impact surface in a plurality of mass-added states which are obtained by affixing respectively a plurality of mass regulating members having known, mutually differing masses to the impact surface; and a restitution coefficient computing portion that obtains, by using the resonance frequencies acquired, a coefficient of restitution for the impact surface when the impact surface is impacted by the golf ball.

According to the present invention, it is possible to find resonance frequencies of the impact surface respectively for the mass added state and the non-mass added state according to whether or not the mass regulating member is affixed, or for the plurality of mass-added states, whereby the coefficient of restitution can be found by using the resonance frequencies with high precision compared to a conventional method. In particular, the parameter that regulates the resonance frequency of the impact surface in the non-mass added state can be found, and the coefficient of restitution can be found by using the parameter with high precision compared to a conventional method.

DETAILED DESCRIPTION OF THE PREFERRED EMBODIMENTS

A method and a device for evaluating restitution characteristics of a golf club head of the present invention are explained in detail below based on preferred embodiments shown in the appended diagrams.

Figure 1:
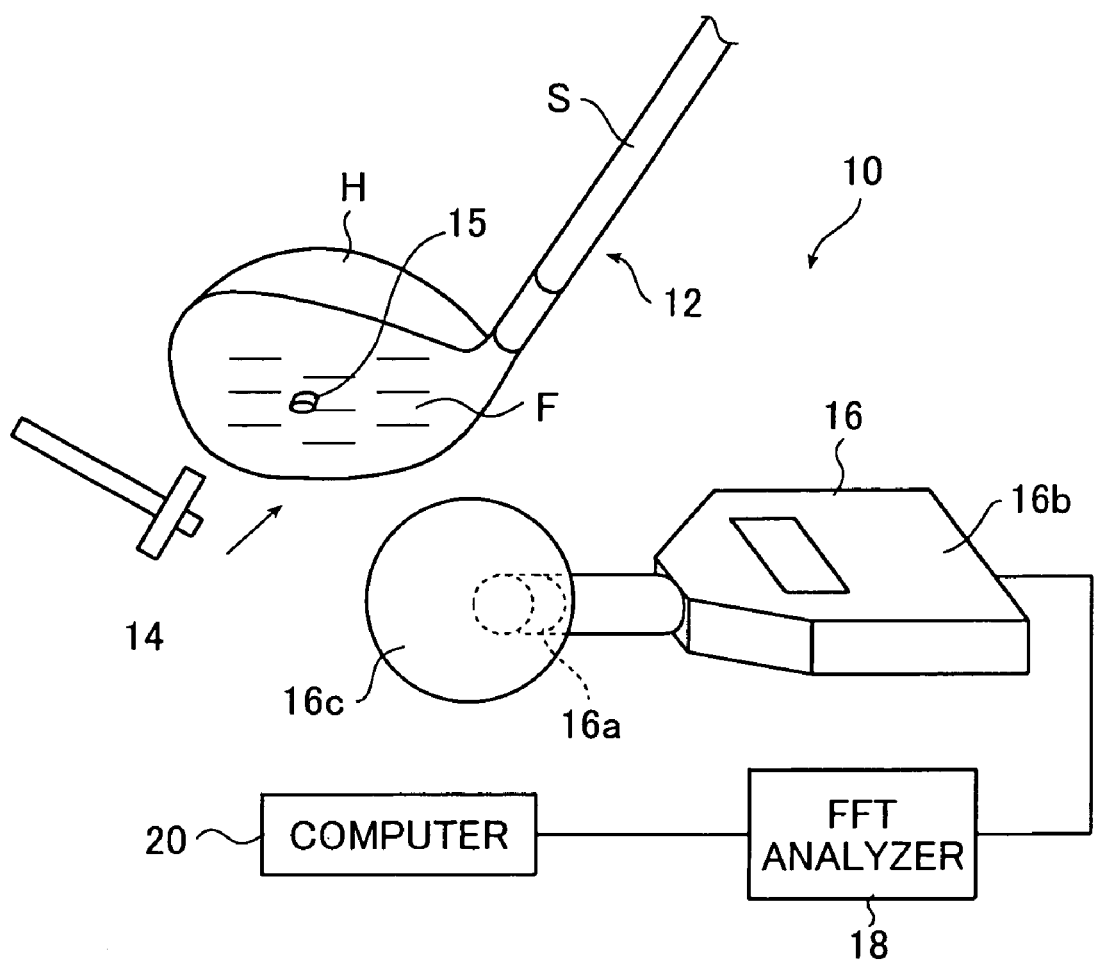
FIG. 1 is a diagram that shows an example of an evaluation system that implements a method of evaluating restitution characteristics of a golf club head according to the present invention.

FIG. 1 shows an evaluation system 10 that implements a method of evaluating restitution characteristics of a golf club of the present invention. A golf club 12 that is evaluated by the evaluation system 10 is a wood type golf club that possesses a hollow golf club head H manufactured out of a metal or the like.

The evaluation system 10 can evaluate the restitution characteristics of an impact surface F with the golf club head H integrated with the golf club as it is, that is, without detaching the golf club head H from a golf club shaft S.

The evaluation system 10 includes an impact vibration jig 14 that performs impact vibration, a mass regulating member 15 that is capable of being freely affixed to a impact surface F of the golf club head H and whose mass is known, a noise measuring device 16, an FFT analyzer 18, and a computer 20.

The impact vibration jig 14 is a jig that performs impact vibration on the impact surface F of the golf club head H. A metallic material that possesses a hardness on an order such that damage is not imparted to the impact surface F is used in a distal end of the jig 14. Further, the impact surface F is lightly impacted by using the impact vibration jig 14 on an order such that damage is not imparted to the impact surface F during impact vibration.

The mass regulating member 15 has a known mass of 1 to 20 g, for example. The mass is preferably from 2 to 10 g. It is possible to freely affix the mass regulating member 15 to the impact surface F by using an adhesive, or the like. The mass regulating member 15 is used in order to change the resonance frequency of the impact surface F according to whether or not the mass regulating member 15 is affixed to the impact surface F, as discussed below.

The noise measuring device 16 is provided with a noise microphone 16a and a noise measurement main unit 16b in a distal end. A wind breaking screen 16c is provided in the circumference of the noise microphone 16a. The noise measuring device 16 uses a known precision noise meter. With the present invention, a noise meter that uses a simple microphone without sound pressure calibration can be used as a substitute for the precision noise meter used in the noise microphone 16a.

The FFT analyzer 18 is an analyzer that performs frequency analysis of a sound pressure signal output from the noise measuring device 16 and finds a first resonance frequency of the impact surface F of the golf club head H. The FFT analyzer 18 forms a resonance frequency computing portion in the present invention. The FFT analyzer 18 uses a known frequency analyzer. The first resonance frequency obtained by the FFT analyzer 18 is sent to the computer 20.

As described below, the computer 20 obtains a modal parameter that specifies the first resonance frequency of the impact surface F in a non-mass added state. The modal parameter is obtained through measurement of the first resonance frequency of the impact surface F in a mass added state, in which the mass regulating member 15 is affixed to the impact surface F, and the first resonance frequency of the impact surface F in a non-mass added state, in which the mass regulating member 15 is not affixed to the impact surface F. In addition, the computer 20 computes a coefficient of restitution e when a golf ball is impacted by the impact surface F. The computation is made from the modal parameter by utilizing a reference table or a relational equation between the modal parameter and the coefficient of restitution e. The computer 20 evaluates the restitution characteristics of the golf club head H, and thus serves as a restitution coefficient computing portion in the present invention.

Further, the computer 20 may also obtain the modal parameter that specifies the first resonance frequency of the impact surface F in a non-mass added state, through measurement of the first resonance frequencies of the impact surface F in a plurality of mass-added states which are obtained by affixing respectively the plural mass regulating members 15 having mutually different masses to the impact surface F. In addition, the computer computes the coefficient of restitution e for when a golf ball is impacted by the impact surface F. The computation is made from the modal parameter by utilizing a reference table of a relational equation between the modal parameter and the coefficient of restitution e. The computer 20 may thus evaluate the restitution characteristics of the golf club head H. In addition, the computer 20 may also compute the coefficient of restitution e by combining the first resonance frequency in the non-mass added state and the modal parameter as computed above, for example. Further, the coefficient of restitution e may also be computed by using the difference between, or the ratio of, the first resonance frequencies in the mass added state and the non-mass added state. The embodiment thus does not limit the method for obtaining the coefficient of restitution e, provided that the method is capable of computing the coefficient of restitution e by using at least the first resonance frequencies in the mass added state and the non-mass added state.

It should be noted that, although the computer 20 configures the evaluation device by software processing that computes the coefficient of restitution e by executing a program, the evaluation device that performs those processings by a dedicated device configured by circuit boards or the like may also be used in the present invention.

In addition, the computer 20 can also carry out the frequency analysis of the FFT analyzer 18 in the present invention. In this case configuration is used in which an A/D converter board that performs A/D conversion of the sound pressure signal output from the noise measuring device is incorporated in the computer 20. The sound pressure signal may also be input directly into the computer 20.

With the evaluation system 10 described above, impact vibration of the impact surface F of the golf club head H is performed first by the impact vibration jig 14. At this point, it is preferable that the golf club 12 be in a state where a hosel portion thereof is suspended in midair while forming a free end. However, a golf club shaft S of the golf club 12 may also be lightly fixed and supported. As described below, any fixing method may be used as long as it does not give any influence on the resonance frequency when the impact surface F of the golf club head H vibrates like a membrane.

On the other hand, an impact sound of the impact surface F during impact vibration is measured from the noise microphone 16a of the noise measuring device 16 disposed in the vicinity of the impact surface F and calibrated in advance by using a pistonphone or the like. The impact sound is output to the FFT analyzer 18 from the noise measuring device 16 as a sound pressure signal.

This type of measurement is performed, for example, in two states. In one state the mass regulating member 15 is affixed to the impact surface F, and in the other state the mass regulating member 15 is not affixed to the impact surface F (a mass added state and a non-mass added state). There are no specific limitations placed on positions at which the mass regulating member 15 is affixed to the impact surface F. For cases of comparing and evaluating the restitution characteristics of a variety of different golf club heads, it is preferable to affix the mass regulating member 15 to substantially the same fixed location of the impact surface F from a viewpoint of performing high-accuracy evaluation of the restitution characteristics. For example, the affixing location may be the substantial geometric center of the impact surface F, or in the vicinity of the geometric center of the impact surface F. Alternatively, the mass regulating member 15 may also be affixed to a location that is an intersection of a straight line passing through the center of gravity of the golf club head H perpendicularly to the impact surface F, and the impact surface F.

The FFT analyzer 18 performs frequency analysis. For example, base band frequency analysis is performed in a band of 0 to 7000 Hz.

Figure 2A:
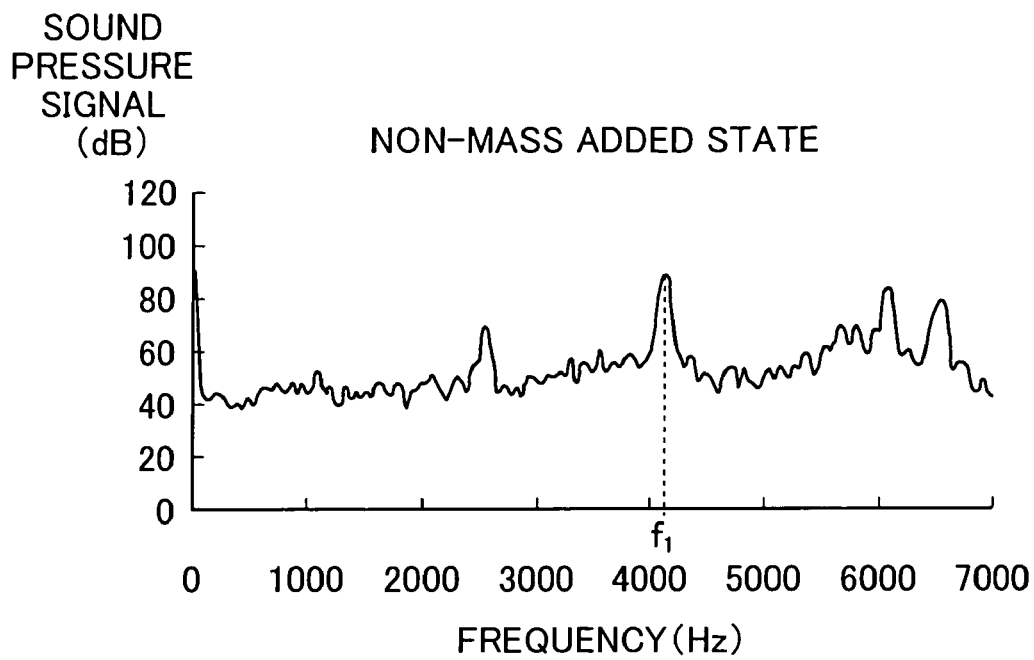
FIG. 2A is a diagram that shows results of frequency analysis of a sound pressure signal obtained by the evaluation system shown in FIG. 1 for a non-mass added state.
Figure 2B:
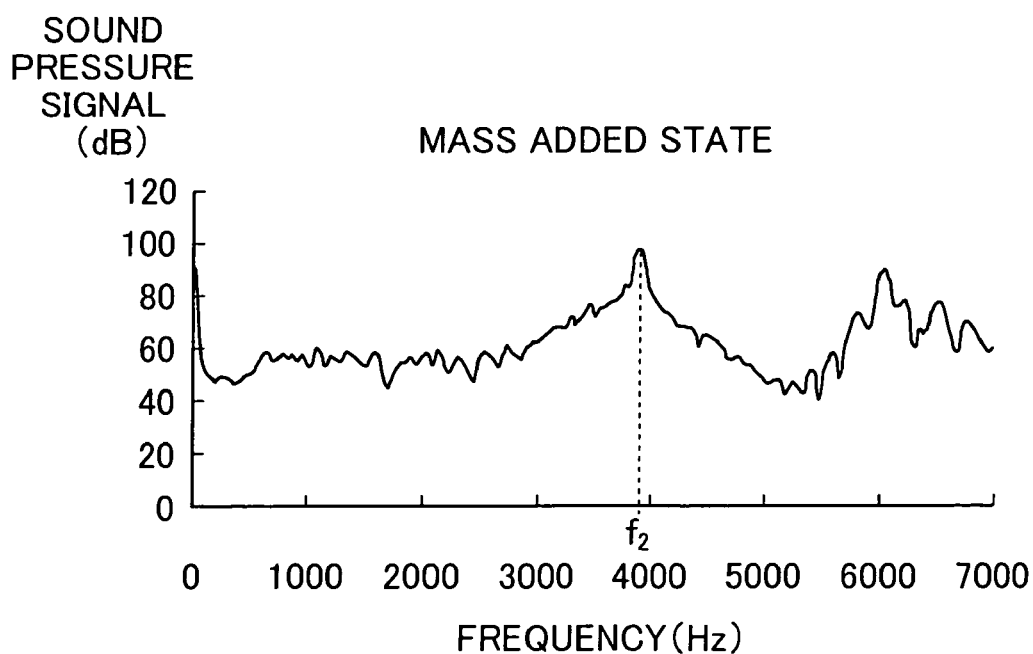
FIG. 2B is a diagram that shows results of frequency analysis of the sound pressure signal obtained by the evaluation system shown in FIG. 1 for a mass added state.

A sound pressure waveform as shown in FIG. 2A, for example, is obtained by frequency analysis. FIG. 2A shows a sound pressure waveform in a non-mass added state. The sound pressure waveform has plural peaks generated in a band from 0 Hz to 7,000 Hz. However, if a first resonance frequency f is restricted in advance to 3,000 to 5,000 Hz, for example, a first resonance frequency $f_1$ in a state where a mass is not added to the impact surface F can be specified from the frequency waveform of the sound pressure signal. Further, a first resonance frequency $f_2$ in a state where a mass is added to the impact surface F can be similarly specified as shown in FIG. 2B.

It should be noted that the first resonance frequency $f_2$ in the mass added state is lower by the mass of the mass regulating member 15 than the first resonance frequency $f_1$ in the non-mass added state.

Further, for cases where this generation band cannot be set in advance, and a first resonance peak cannot be specified, the first resonance peak may be specified by a method described below.

That is, the first resonance frequencies $f_1$ and $f_2$ exist in a frequency band of several thousands of hertz bandwidth, and therefore the fact that information on the first resonance peak is also contained in vibrations of the impact surface F as well as the sound pressure signal, is utilized.

Figure 3:
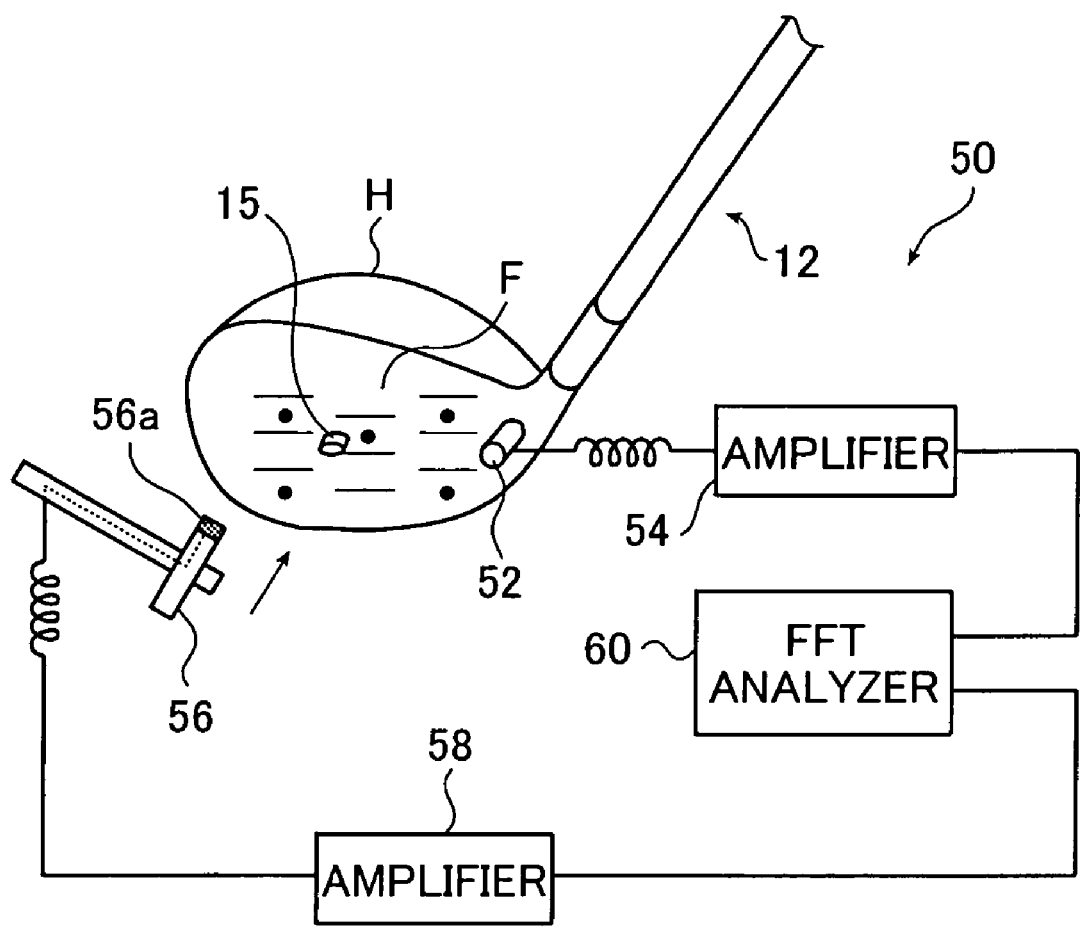
FIG. 3 is a diagram that shows an example of another evaluation system that implements the method of evaluating restitution characteristics of a golf club head according to the present invention.

FIG. 3 shows an evaluation system 50 that is different from the evaluation system 10 shown in FIG. 1.

As shown in FIG. 3, an acceleration pickup 52 having a mass equal to or less than 1 g, for example, is affixed to the impact surface F of the golf club head H, and the evaluation system 50 performs impact vibration of the impact surface F by using an impact hammer 56. The acceleration pickup 52 is an Endevco Corporation Model 22 having a mass of 0.14 g, for example. It should be noted that the acceleration pickup 52 is affixed to a location in an edge portion of the impact surface F with little influence on vibrations of the impact surface F. For cases where the mass of the acceleration pickup gives an influence on vibrations of the impact surface F at an unignorable level, the acceleration pickup 52 may be affixed in the vicinity of the position at which the mass regulating member 15 is affixed in order to take the acceleration pickup 52 and the mass regulating member 15 as one mass regulating member, as described below.

The acceleration signal obtained from the acceleration pickup 52, through an amplifier 54, and an impact vibration signal of an impact vibration force obtained, through an amplifier 56, by using the impact hammer to measure the impact vibration force of impact vibration are input to the FFT analyzer 60. A function of the acceleration signal with respect to the impact force for the impact vibration, that is, a transfer function, is obtained by the FFT analyzer 60. Transfer functions are obtained by applying impact forces of the impact vibration hammer 56 at plural points distributed on the impact surface F of the golf club head H (impact vibration is performed at locations shown by solid circles on the impact surface F in FIG. 3, for example). Sharp peaks according to shapes in the vibration deflection at the first resonance frequency of the impact surface F with the same phase appear in the plurality of transfer functions thus obtained, regardless of the impact points for impact vibration. The frequency of the peak location can be extracted as the first resonance frequency. FIG. 3 shows an example of finding the first resonance frequency $f_2$ in the mass added state. In addition, the first resonance frequency $f_1$ in the non-mass added state can be found by removing the mass regulating member 15 from the impact surface F.

The processings of the FFT analyzer 60 for finding the transfer function can also be executed by the computer in the evaluation system 50. In this case an A/D converter board that performs A/D conversion on the sound pressure signal output from a noise measuring device is incorporated in the computer, and the impact vibration signal and the acceleration signal may be input into the computer.

Figure 4:
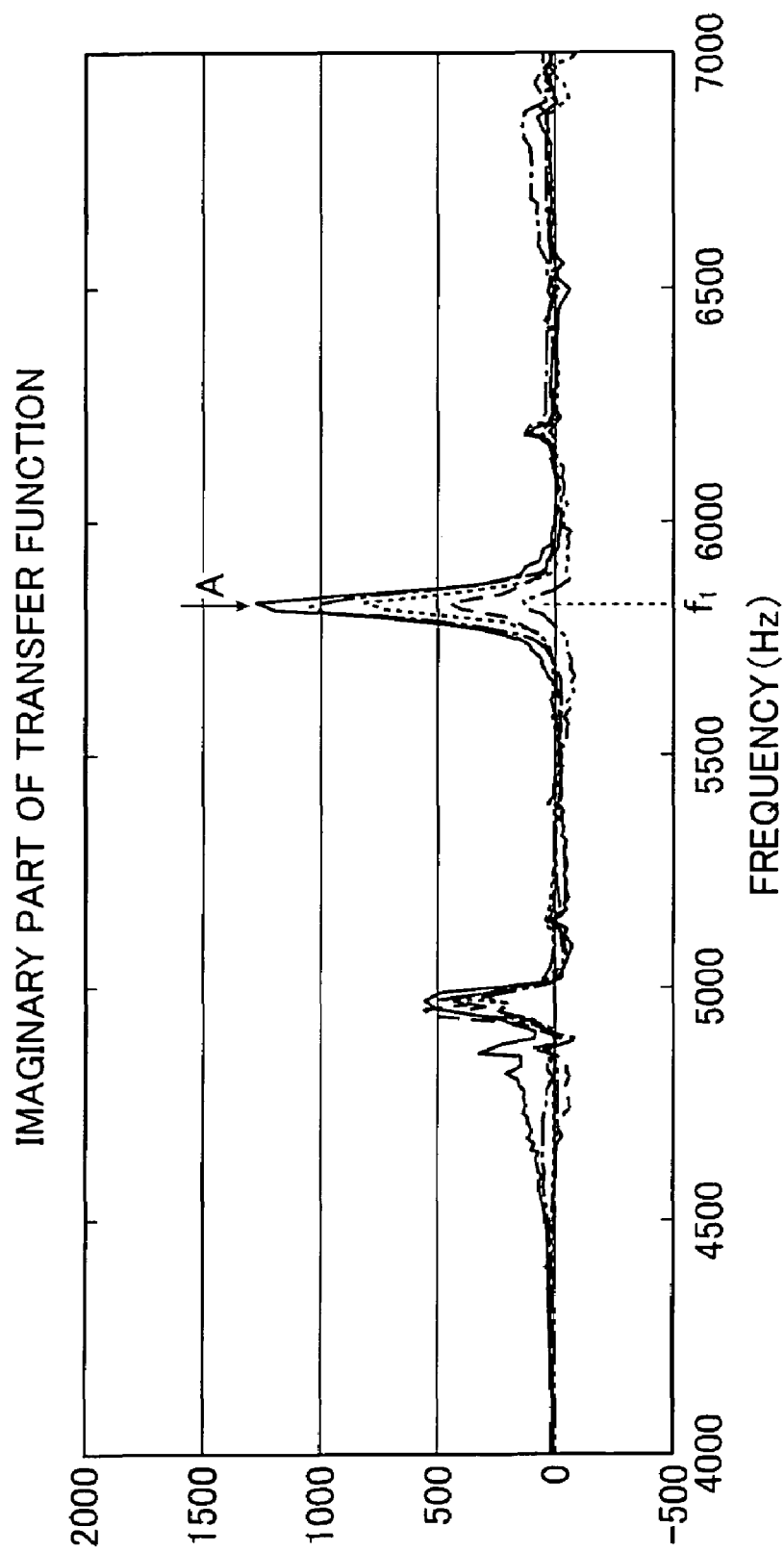
FIG. 4 is a diagram that shows an example of a waveform of an imaginary part of a transfer function obtained by the evaluation system shown in FIG. 3.

FIG. 4 shows imaginary parts of transfer functions when the impact vibrations are performed at five different points on the impact surface F in the state where the mass is not added to the impact surface F. A golf club head that differs from the golf club head shown in FIGS. 2A and 2B is used here. It is thus understood that the imaginary parts have a sharp, maximum peak at a location A in each of the five transfer functions, forming a resonance peak. The frequency of the location A is the first resonance frequency $f_1$, and is equal to 5820 Hz.

Further, the peak frequency of the sharp peak of the transfer functions having the same phase, regardless of the impact point for impact vibration, may also be obtained as the first resonance frequency $f_1$. The reason why the first resonance frequency $f_1$ can thus be found by determining the sharp peaks at the same phase is that the shape of the vibration deflection at the first resonance frequency forms in a manner that the impact surface F deforms uniformly to protrude out, or be depressed, in a direction perpendicular to the impact surface F like a membrane.

The resonance peak due to the first resonance peak from among the plurality of peaks shown in FIG. 2 can thus be specified by utilizing the transfer functions. The first resonance frequencies $f_1$ and $f_2$ in the mass added state and in the non-mass added state can thus be found. The golf club head shown in FIGS. 2A and 2B is different from the golf club head shown in FIG. 4. The first resonance frequency $f_1$ shown in FIG. 2A and the first resonance frequency $f_2$ shown in FIG. 4 are therefore different.

It should be noted that the first resonance frequencies $f_1$ and $f_2$ can be found accurately from transfer functions obtained by measuring the acceleration signal. However, the first resonance frequencies $f_1$ and $f_2$ may also be found from the sound pressure waveform of the sound pressure signal in a frequency band determined in advance.

Furthermore, the first resonance frequencies $f_1$ and $f_2$ may also be found from the waveform of the acceleration signal obtained by attaching the acceleration pickup 52 to the impact surface F of the golf club head and performing impact vibration using the impact vibration jig 14. In this case, specifying the first resonance frequencies $f_1$ and $f_2$ may be performed similarly to the method of specifying the first resonance frequencies $f_1$ and $f_2$ from the sound pressure signal described above.

It should be noted that although the transfer function and the first resonance frequency are found for each impact points in the example shown in FIG. 4, the transfer functions obtained at each of the impact points may also be averaged and expressed as one transfer function. The maximum peak obtained from the averaged transfer function may then be used as the first resonance peak to specify the first resonance frequency.

Figure 5:
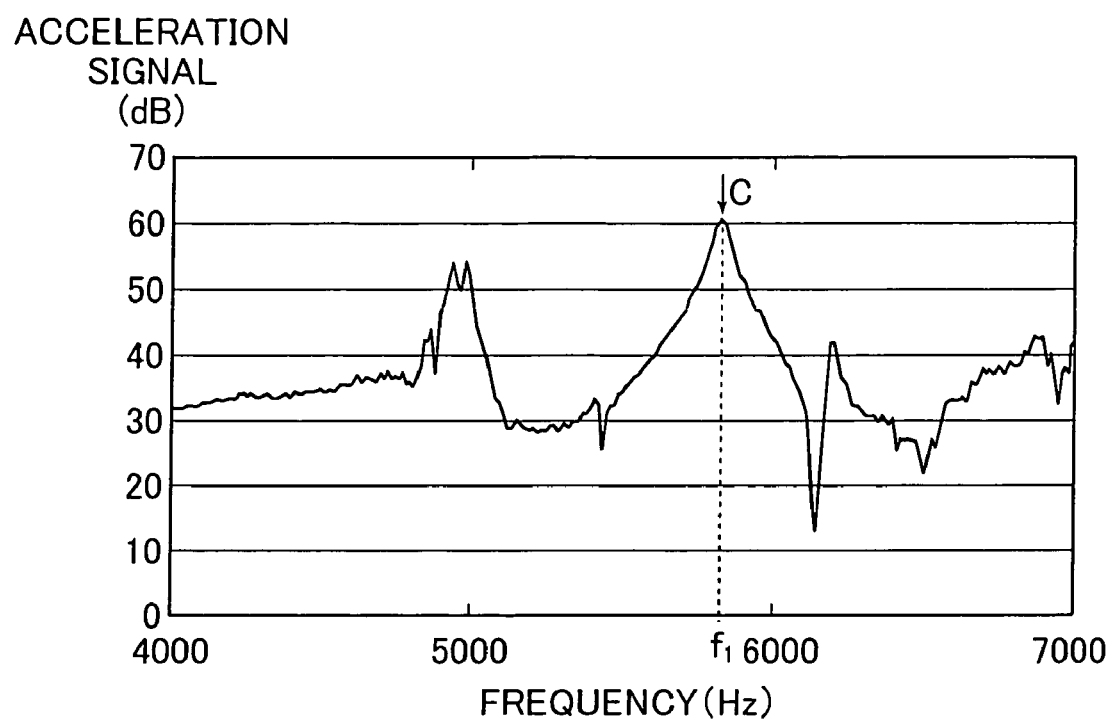
FIG. 5 is a diagram that shows an example of frequency analysis results on an acceleration signal by the evaluation system shown in FIG. 3.

FIG. 5 shows an example of a waveform of an acceleration signal in a non-mass added state that is obtained by the system shown in FIG. 3. The first resonance peak is formed in a location C.

The first resonance frequencies $f_1$ and $f_2$, which are found in two states according to whether or not the mass regulating member 15 is affixed, are sent to the computer 20.

A modal parameter m (referred to as a dynamic mass or a modal mass) and a modal parameter k (referred to as a dynamic spring constant or a modal stiffness) in the first resonance mode are computed by the computer 20 using Eqs. (1) and (2) below.

$$2\pi \times f_1 = (k/m)^{(1/2)} \quad (1)$$

$$2\pi \times f_2 = (k/(m+\Delta m))^{(1/2)} \quad (2)$$

where Δm is the known mass of the mass regulating member 15, and π is equal to the ratio of the circumference of a circle to its diameter.

The first resonance frequency can thus be specified by Eq. (1) and Eq. (2). This is because the first resonance mode in the first resonance frequencies $f_1$ and $f_2$ has a mode in which the impact surface F deforms according to simple vibrations to uniformly protrude out, or be depressed, in a direction perpendicular to the impact surface F like a membrane with a location in the vicinity of the geometric center of the impact surface F taken as the position of maximum displacement. Accordingly, the modal parameters m and k thus obtained substantially correspond to the dynamic mass and the dynamic spring constant used to determine the actual first resonance frequency of the impact surface F of the golf club head H.

The modal parameters m and k that are expressed by Eqs. (1) and (2) are obtained by the computer 20 using the obtained first resonance frequencies $f_1$ and $f_2$. In addition, the coefficient of restitution e for a golf ball is estimated by using the modal parameter k of the two modal parameters m and k and utilizing an equation or a reference table set up in advance within the computer 20.

The coefficient of restitution e of the golf ball can thus be estimated by using the modal parameter k because it has been found that a correlation between the modal parameter k and the coefficient of restitution e is a much stronger correlation compared to a correlation between the first resonance frequency and the coefficient of restitution, which is used in a conventional estimation method. For example, a correlation between the modal parameter k and the coefficient of restitution e of various types of golf club heads having a non-uniform thickness structure in which the thickness of a impact surface of the golf club head changes, depending on position, is improved compared to the conventional correlation.

Figure 6:
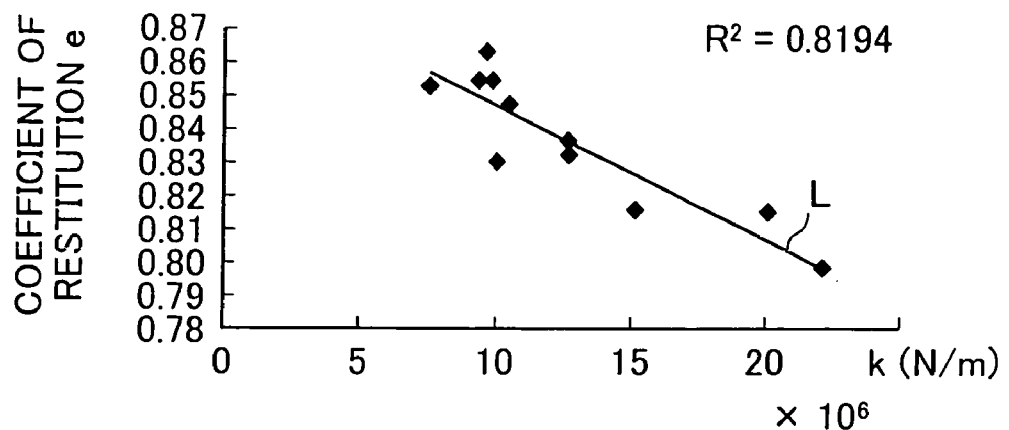
FIG. 6 is a diagram that shows an example of a relationship between a parameter obtained by the method of evaluating restitution characteristics of a golf club head according to the present invention and a coefficient of restitution.

An example of a relationship between the modal parameter k and the coefficient of restitution e is shown in FIG. 6. An example of a relationship between the first resonance frequency $f_1$ and the coefficient of restitution e is shown in FIG. 7.

Solid diamond-shaped symbols in FIG. 6 indicate a relationship between the coefficient of restitution e and the modal parameter k that specifies the first resonance frequency of the impact surface F in the non-mass added state for various golf club heads, including the one with the non-uniform thickness structure in which the thickness of the impact surface F changes depending upon location. As shown in FIG. 6, it can be understood that the relationship between the modal parameter k and the coefficient of restitution e has a correlation coefficient $R^2$ equal to 0.8194 by linear regression.

Figure 7:
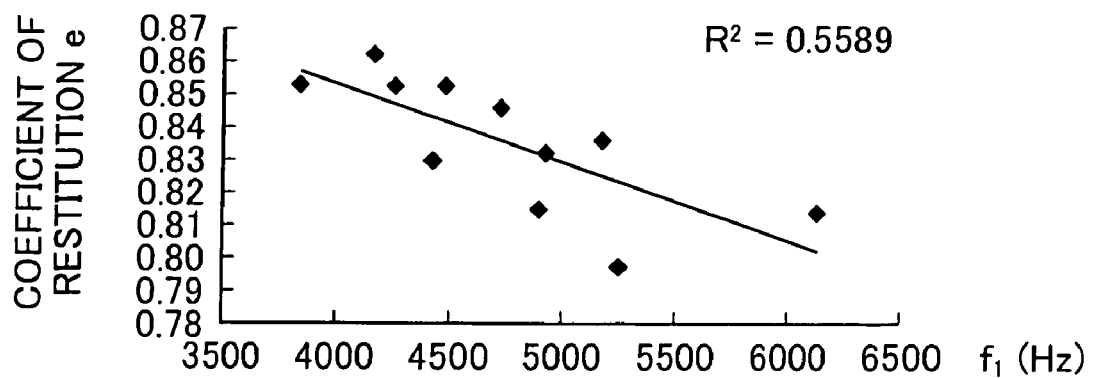
FIG. 7 is a diagram that shows an example of a relationship between a parameter obtained by a conventional method of evaluating restitution characteristics of a golf club head and a coefficient of restitution.

On the other hand, solid diamond-shaped symbols in FIG. 7 show a relationship between the coefficient of restitution e and the first resonance frequency $f_1$ of the impact surface F (first resonance frequency in a non-mass added state) for various golf club heads, including the one with the non-uniform thickness structure in which the thickness of the impact surface F changes depending upon location. As shown in FIG. 7, the relationship between the first resonance frequency $f_1$ and the coefficient of restitution e has a correlation coefficient $R^2$ equal to 0.5589 by linear regression.

It can thus be understood that a linear regression equation L that expresses the relationship between the coefficient of restitution e and the modal parameter k shown in FIG. 6 has a much stronger correlation compared to the linear regression equation that expresses the relationship between the coefficient of restitution e and the first resonance frequency $f_1$ shown in FIG. 7. Therefore the coefficient of restitution e can be estimated from the modal parameter k by utilizing the linear regression equation L or a reference table made based on the linear regression equation L, and can be estimated with higher accuracy than when using a conventional method.

An evaluation of whether or not the coefficient of restitution e complies with the rules determined by the USGA, that is, whether or not the coefficient of restitution e is equal to or less than 0.830, can thus be performed by storing the linear regression equation L, or the reference table made based on the linear regression equation L, in advance in the computer 20, and estimating the coefficient of restitution e by utilizing the linear regression equation or the reference table.

Furthermore, in this embodiment, the first resonance frequency of the impact surface F is obtained for the mass added state and the non-mass added state, and the modal parameter k is computed based on the first resonance frequencies. However, the first resonance frequencies may also be found in states where two or more different masses are respectively added by affixing to the impact surface F two or more mass regulating members having different masses. The modal parameter that specifies the first resonance frequency of the impact surface in the non-mass added state may then be computed by using the first resonance frequencies of the impact surface.

Further, the mass of the acceleration pickup 52 is known. For cases where the mass is large enough to give an influence on vibration of the impact surface F, the first resonance frequencies may be obtained in two states as described below by using the acceleration signal obtained from the acceleration pickup 52 described above. The modal parameter that specifies the first resonance frequency in the non-mass added state may then be found from the first resonance frequencies. The acceleration pickup 52 is affixed to a center location or the like of the impact surface F as one mass regulating member, thus obtaining a first mass added state. In addition, the mass regulating member 15 is affixed in the vicinity of the location at which the acceleration pickup 52 is affixed, thus obtaining a second mass added state. The first resonance frequensies are obtained in the states where two different masses are respectively added, and the modal parameter that specifies the first resonance frequency of the impact surface in the non-mass added state is computed.

It should be noted that, although the modal parameter k is used for estimating the coefficient of restitution e in this embodiment, the linear regression equation found by linear regression of a relationship between the coefficient of restitution e and the reciprocal of the modal parameter k or a reference table that is formed based on the linear regression equation, may be utilized in estimating the coefficient of restitution e. That is, the coefficient of restitution e may also be estimated by using the reciprocal of the modal parameter k. In addition, the coefficient of restitution e may also be estimated by using the dynamic mass m.

Additionally, a correspondence between the coefficient of restitution e and values obtained by arithmetical operation of the modal parameters are operated arithmetically may also be formed, and a linear equation or a reference table that expresses the correspondence may be made. The coefficient of restitution e may then be estimated by utilizing the equation or the reference table. Any of the modal parameters may be used provided that computations can be made using the modal parameter specifying the first resonance frequency of the impact surface F and obtained from two states including a state in which the mass regulating member 15 is affixed and a state in which the mass regulating member 15 is not affixed. Furthermore, in addition to mass parameters and stiffness parameters, the modal parameter may also refer to damping parameters that contribute to the first resonance frequency and to damping of the first resonance frequency.

It should be noted that the first resonance frequency is used as the resonance frequency in the present invention because the first vibration mode of the impact surface F is similar to deformation of the impact surface F when the impact surface F strikes a golf ball.

In addition, it is preferable to compute the coefficient of restitution e by using the first resonance frequency $f_1$ and the modal parameter k in order to perform the computation more accurately. The coefficient of restitution e can be computed more accurately by using the first resonance frequency $f_1$ and the modal parameter k irrespective of the distinction between the above-mentioned non-uniform thickness structure and a uniform thickness structure in which the thickness of the impact surface F is uniform in any location. That is, the coefficient of restitution e is computed by Eq. (3) below by using predetermined coefficients a, b, and c.

Coefficient of restitution $e = a \cdot f_1 + b \cdot k + c$ \hfill (3)

Figure 8A:
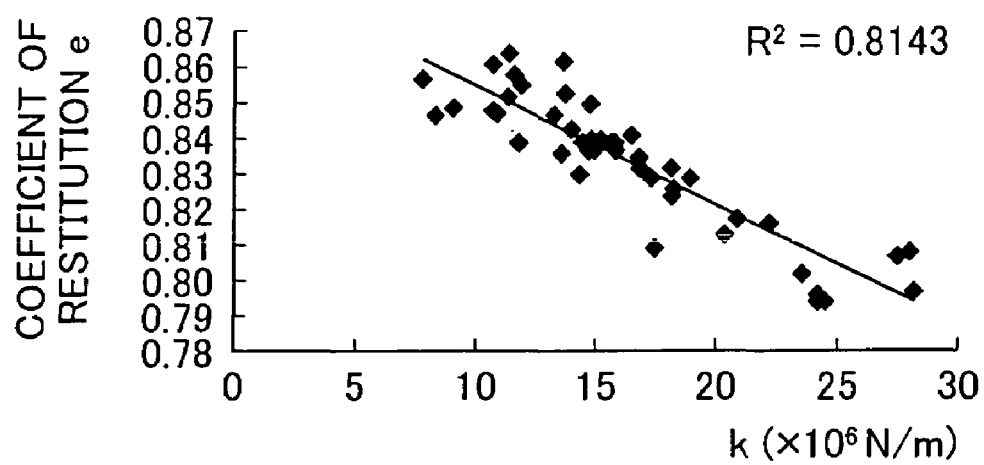
FIG. 8A is a scatter diagram of an example that expresses a correlation between a coefficient of restitution of a golf club head and a modal parameter.
Figure 8B:
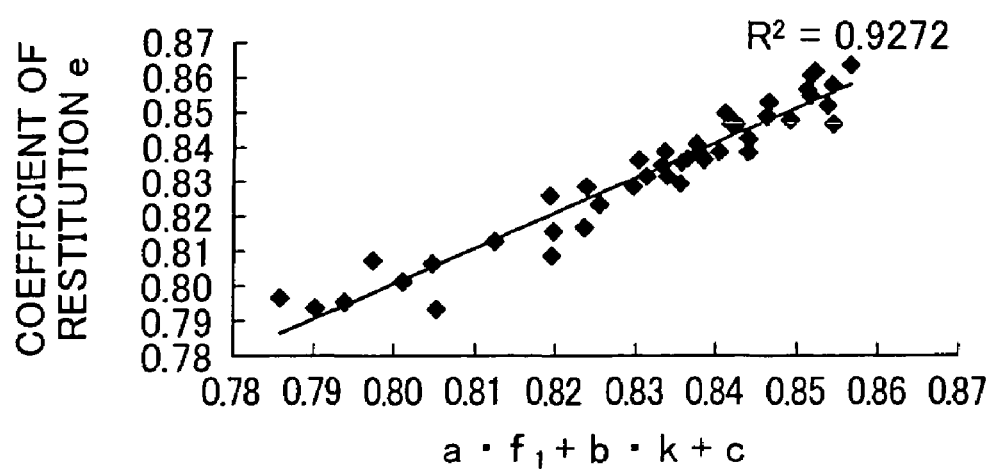
FIG. 8B is a scatter diagram of an example that expresses a correlation between a coefficient of restitution of a golf club head and a value expressed by Eq. (3)

FIG. 8A is a scatter diagram that expresses a correlation between the coefficient of restitution e and the modal parameter k for 13 types of golf club heads on sale having non-uniform thickness structures, and 32 types of golf club heads on sale having uniform structures, thus for a total of 45 types of golf club heads. FIG. 8B is a scatter diagram that expresses a correlation between the coefficient of restitution e and values computed by the right hand side of Eq. (3).

The correlation coefficient $R^2$ between the coefficient of restitution e and the values computed by the right hand side of Eq. (3) is 0.927. It can thus be understood that a very good correspondence can be attained irrespective of the distinction between non-uniform thickness structures and uniform thickness structures.

Figure 9A:
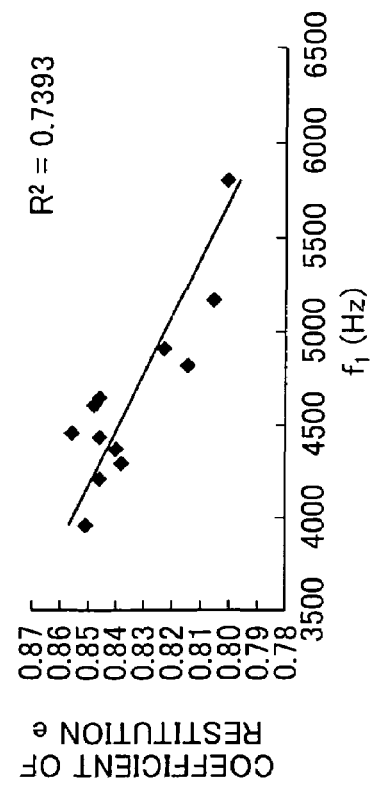
FIGS. 9A and 9B are scatter diagrams of another example that express a correlation between a coefficient of restitution of a golf club head and a first resonance frequency.
Figure 9C:
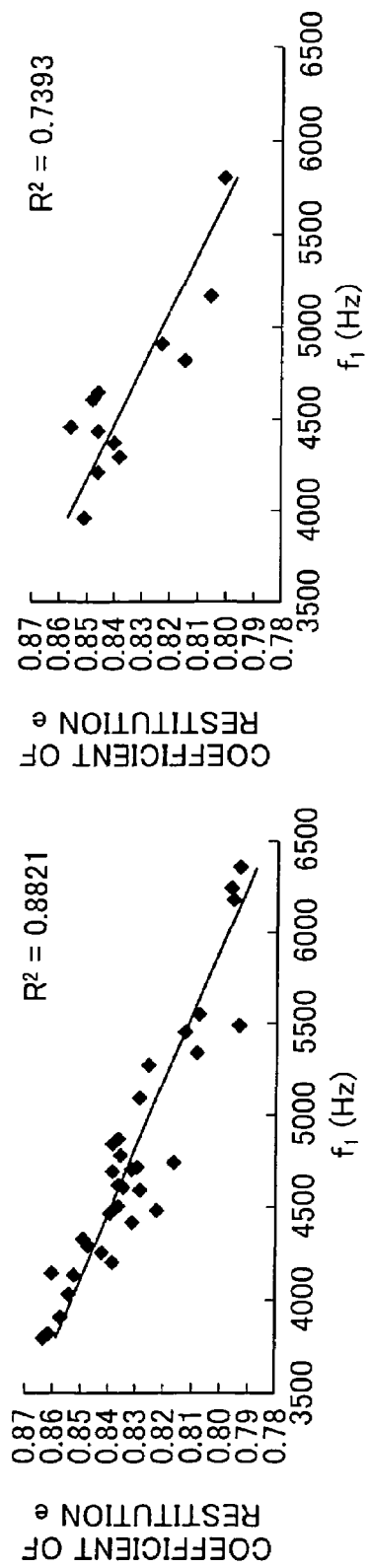
FIGS. 9C and 9D are scatter diagrams of another example that express a correlation between a coefficient of restitution of a golf club head and a modal parameter.
Figure 9B:
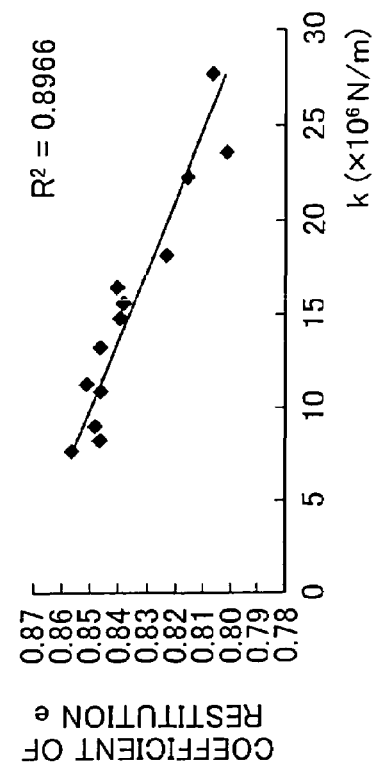
Figure 9D:
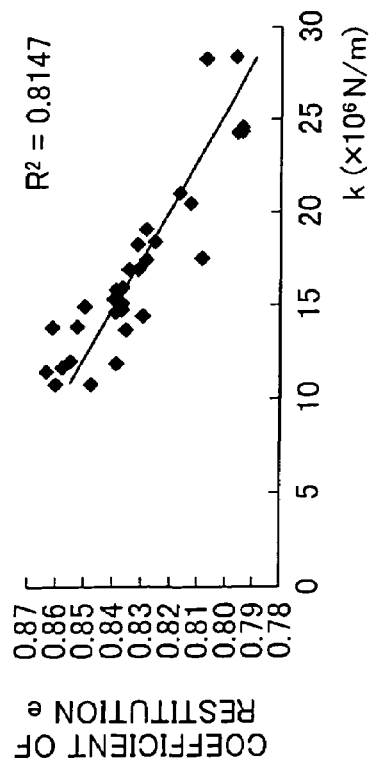

FIG. 9A is a scatter diagram that expresses a correlation between the coefficient of restitution e and the conventional first resonance frequency $f_1$ for the 32 types of golf club heads on sale having a uniform thickness structure described above. FIG. 9B is a scatter diagram that expresses a correlation between the coefficient of restitution e and the modal parameter k for the 32 types of golf club heads on sale having a uniform thickness structure described above. Further, FIG. 9C is a scatter diagram that expresses a correlation between the coefficient of restitution e and the conventional first resonance frequency $f_1$ for the 13 types of golf club heads on sale having a non-uniform thickness structure described above. FIG. 9D is a scatter diagram that expresses a correlation between the coefficient of restitution e and the modal parameter k for the 13 types of golf club heads on sale having a non-uniform thickness structure described above.

From the scatter diagrams of FIGS. 9C and 9D, as for the coefficient of restitution e of the golf club heads having the non-uniform thickness structure, the correlation coefficient $R^2$ is equal to 0.8966 with respect to the modal parameter k (refer to FIG. 9D), and is equal to 0.7393 with respect to the first resonance frequency $f_1$ (refer to FIG. 9C). The correlation with the modal parameter k is thus higher than the correlation with the first resonance frequency $f_1$. On the other hand, from the scatter diagrams of FIGS. 9A and 9B, as for the coefficient of restitution e of the golf club heads having the uniform thickness structure, the correlation coefficient $R^2$ is equal to 0.8147 with respect to the modal parameter k (refer to FIG. 9B), and is equal to 0.8821 with respect to the first resonance frequency $f_1$ (refer to FIG. 9B). The correlation with the modal parameter k is thus lower than the correlation with the first resonance frequency $f_1$. Therefore, in order to compute the coefficient of restitution e with higher accuracy, it is necessary to use the first resonance frequency $f_1$ for uniform thickness structures and use the modal parameter k for non-uniform thickness structures. That is, it becomes necessary to use a different computation depending upon the structure of the golf club head. However, the method of computing the coefficient of restitution e by using Eq. (3) as described above provides a very high correlation, with the correlation coefficient $R^2$ equal to 0.9272 as shown in FIG. 8B. Accordingly, it is not necessary to change the method for computing the coefficient of restitution e depending upon the structure of the golf club head. The coefficient of restitution e can be found by using the value of the right hand side of Eq. (3).

The restitution characteristics can thus be evaluated by performing impact vibration on the impact surface F with the golf club 12 in a state where the hosel portion of the golf club 12 is suspended in midair, or is lightly supported, measuring the sound pressure signal during the impact vibration, obtaining the first resonance frequencies $f_1$ and $f_2$ in the mass added state and the non-mass added state, and using the first resonance frequencies $f_1$ and $f_2$ in estimating the coefficient of restitution e at a higher accuracy that that of a conventional method. Moreover, it is unnecessary to remove the golf club shaft S from the golf club head H. Therefore, a judgement can be made easily and with good accuracy as to whether or not a golf club used in a golf competition does not comply with the regulations regarding the coefficient of restitution, and this judgement can be made within a limited time period before the competition starts.

Further, for cases where a golf club manufacturer manufactures a lot of identical golf clubs 12, the coefficient of restitution e can be inspected easily in a short amount of time and with good accuracy using two states whether or not the mass regulating member 15 is affixed. The inspection can be performed with the golf clubs 12 as finished products in which the golf club shaft S and the golf club head H are integrated with each other. A process for inspecting the product performance of the golf clubs 12 can thus be made simple, and fluctuation of the product performance of the golf clubs 12 that are actually shipped for sale can be reduced.

In this embodiment, the parameter that specifies the first resonance frequency is found from the first resonance frequencies $f_1$ and $f_2$ of the impact surface F of the golf club head H, and the coefficient of restitution e is estimated using this parameter. In addition, the mass regulating member 15 is affixed to the impact surface F at a variety of locations on the impact surface F, and the two resonance frequencies are found at each location respectively for a case where the mass regulating member 15 is affixed and a case where it is not affixed. By determining a distribution of the parameter on the impact surface F from the two resonance frequencies, a distribution of a coefficient of restitution e in the impact surface F can be found. In general, the resonance frequency changes greatly at portions having a large deflection amplitude at resonant mode due to the mass regulating member 15 being affixed. The distribution of deflection amplitudes due to vibrations of the impact surface F (deformation distribution) can thus be easily found by measuring differences in the resonance frequency of the impact surface F between the mass added state and the non-mass added state. In addition, the coefficient of restitution distribution on the impact surface F can be easily found from the above distribution.

With the method of the present invention, the coefficient of restitution e of the golf club head H can be estimated with high reliability compared to a conventional method. On the market, by including information relating to characteristics of the golf club 12 to sell, or by including the coefficient of restitution e of the golf club 12 that is estimated by the method of the present invention, effective information can be provided to a golfer who purchases the golf club 12. Further, the information relating to the characteristics of the golf club 12, including the coefficient of restitution e of the golf club 12 that is estimated by the method of the present invention, can be shown on a tag, a seal, or the like attached to the golf club 12. The golfer understands the information, grasp the characteristics of the golf club 12 and finally purchases.

The method and device for evaluating the characteristics of a golf club head according to the present invention are explained in detail above. However, the present invention is not limited to the above embodiments. Various improvements and changes may of course be made within a scope not departing from the gist of the present invention. For example, it is not necessary to use one mass regulating member in the present invention. The resonance frequency may be obtained for a state in which two or more masses are added, by using a plurality of mass regulating members having different masses and for a non-mass added state. A parameter that specifies the resonance frequency in the non-mass added state may then be computed with good accuracy, thereby obtaining the coefficient of restitution e.

What is claimed is:

1. A method of evaluating restitution characteristics of a golf club head by performing impact vibration through application of an external force to a golf ball impact surface of the golf club head, the method comprising:
   acquiring a resonance frequency of the impact surface in a mass added state, which is obtained by affixing a mass regulating member having a known mass to the impact surface, and acquiring a resonance frequency of the impact surface in a non-mass added state, in which the mass regulating member is not affixed to the impact surface, by using a response signal of the impact surface due to the impact vibration; and
   computing, by using the resonance frequency obtained in the mass added state and the resonance frequency in the non-mass added state, a coefficient of restitution for the impact surface when the impact surface impacts a golf ball.

2. The method of evaluating restitution characteristics of a golf club head according to claim 1, further comprising, when computing the coefficient of restitution, obtaining a parameter that specifies the resonance frequency of the impact surface in the non-mass added state, in which the mass regulating member is not affixed to the impact surface, and computing the coefficient of restitution of the impact surface when the impact surface impacts a golf ball by using the parameter.

3. The method of evaluating restitution characteristics of a golf club head according to claims 1, wherein the resonance frequency is a first resonance frequency of the impact surface.

4. The method of evaluating restitution characteristics of a golf club head according to claim 2, wherein the parameter is a modal parameter of a resonance mode of the impact surface.

5. The method of evaluating restitution characteristics of a golf club head according to claim 4, further comprising, when computing the coefficient of restitution, obtaining a modal parameter, the modal parameter being one of a modal mass and a modal stiffness, and using the modal parameter to compute the coefficient of restitution.

6. The method of evaluating restitution characteristics of a golf club head according to claims 3, wherein the response signal is an acceleration signal of vibrations of the impact surface.

7. The method of evaluating restitution characteristics of a golf club head according to claim 6, further comprising: performing the impact vibration by applying the external force at plural points that are distributed on the impact surface; obtaining, for each of the points, a transfer function for an acceleration signal with respect to the external force; and acquiring as the first resonance frequency of the impact surface a peak frequency at which a peak forms in an identical phase in each obtained transfer function.

8. The method of evaluating restitution characteristics of a golf club head according to claim 1, wherein the response signal is a sound pressure signal of the impact surface.

9. A method of evaluating restitution characteristics of a golf club head by performing impact vibration through application of an external force to a golf ball impact surface of the golf club head, the method comprising:
   acquiring resonance frequencies of the impact surface in a plurality of mass-added states, which are obtained by affixing respectively a plurality of mass regulating members having known, mutually differing masses to the impact surface, by using a response signal of the impact surface due to the impact vibration; and
   computing, by using the resonance frequencies acquired in a plurality of mass-added states, a coefficient of restitution for the impact surface when the impact surface impacts a golf ball.

10. The method of evaluating restitution characteristics of a golf club head according to claim 9, further comprising, when computing the coefficient of restitution, obtaining a parameter that specifies the resonance frequency of the impact surface in the non-mass added state, in which the mass regulating member is not affixed to the impact surface, and computing the coefficient of restitution of the impact surface when the impact surface impacts a golf ball by using the parameter.

11. The method of evaluating restitution characteristics of a golf club head according to claims 9, wherein the resonance frequency is a first resonance frequency of the impact surface.

12. The method of evaluating restitution characteristics of a golf club head according to claim 10, wherein the parameter is a modal parameter of a resonance mode of the impact surface.

13. The method of evaluating restitution characteristics of a golf club head according to claim 12, further comprising, when computing the coefficient of restitution, obtaining a modal parameter, the modal parameter being one of a modal mass and a modal stiffness, and using the modal parameter to compute the coefficient of restitution.

14. The method of evaluating restitution characteristics of a golf club head according to claim 12, wherein the response signal is an acceleration signal of vibrations of the impact surface.

15. The method of evaluating restitution characteristics of a golf club head according to claim 14, further comprising: performing the impact vibration by applying the external force at plural points that are distributed on the impact surface; obtaining, for each of the points, a transfer function for an acceleration signal with respect to the external force; and acquiring as the first resonance frequency of the impact surface a peak frequency at which a peak forms in an identical phase in each obtained transfer function.

16. The method of evaluating restitution characteristics of a golf club head according to claims 9, wherein the response signal is a sound pressure signal of vibrations of the impact surface.

17. A device for evaluating restitution characteristics of a golf club head, the device evaluating the restitution characteristics of the golf club head by using a response signal of a golf ball impact surface of a golf club when impact vibration is performed on the impact surface by applying an external force to the impact surface, the device comprising:

a resonance frequency computing portion that acquires a resonance frequency of the impact surface in a mass added state, which is obtained by affixing a mass regulating member having a known mass to the impact surface, and a resonance frequency of the impact surface in a non-mass added state, in which the mass regulating member is not affixed to the impact surface, by using a response signal of the impact surface due to the impact vibration; and a restitution coefficient computing portion that obtains, by using the resonance frequency in the mass added state and the resonance frequency in the non-mass added state, a coefficient of restitution for the impact surface when the impact surface is impacted by the golf ball.

18. A device for evaluating restitution characteristics of a golf club head, the device evaluating the restitution characteristics of the golf club head by using a response signal of a golf ball impact surface of a golf club when impact vibration is performed on the impact surface by applying an external force to the impact surface, the device comprising:

a resonance frequency computing portion that acquires resonance frequencies of the impact surface by using a response signal of the impact surface due to the impact vibration, with the impact surface in a plurality of mass-added states which are obtained by affixing respectively a plurality of mass regulating members having known, mutually differing masses to the impact surface; and a restitution coefficient computing portion that obtains, by using the resonance frequencies acquired, a coefficient of restitution for the impact surface when the impact surface is impacted by the golf ball.

* * * * *